United States Patent [19]

Goodman et al.

[11] Patent Number: 5,145,777
[45] Date of Patent: Sep. 8, 1992

[54] PLANT CELLS RESISTANT TO HERBICIDAL GLUTAMINE SYNTHETASE INHIBITORS

[75] Inventors: Howard M. Goodman, Newton Centre, Mass.; Gunter Donn, Hofheim, Fed. Rep. of Germany

[73] Assignee: The General Hospital Corporation, Boston, Mass.

[21] Appl. No.: 700,116

[22] Filed: May 9, 1991

Related U.S. Application Data

[63] Continuation of Ser. No. 399,420, Aug. 28, 1989, abandoned, which is a continuation-in-part of Ser. No. 81,455, Aug. 4, 1987, abandoned, which is a continuation-in-part of Ser. No. 833,156, Feb. 27, 1986, abandoned, which is a continuation-in-part of Ser. No. 742,846, Jun. 10, 1985, abandoned, which is a continuation-in-part of Ser. No. 656,488, Oct. 1, 1984, abandoned.

[51] Int. Cl.$^5$ .................. C12N 5/04; C12N 15/00; A01H 4/00; A01H 1/06
[52] U.S. Cl. .................. 435/172.3; 435/320.1; 435/240.4; 435/69.1; 800/200; 800/205; 800/255; 536/27; 71/65; 935/33; 935/35
[58] Field of Search .................. 435/172.3, 320.1, 240.4, 435/69.1, 33, 35; 47/58; 800/200, 205, 255; 536/27; 71/65

[56] References Cited

U.S. PATENT DOCUMENTS 4,443,971 4/1984 Chaleff .................. 47/58

OTHER PUBLICATIONS

Goodman et al. (1987), Science 236, 48–54.
Herrera-Estrella et al. (1983), Nature 303:816–820.
Fraley et al. (1983) Proc. Natl. Acad. Science 80:4803–4807.
Goodman et al. (1984) J. Cell Biochem. Abst. Supplement 8B-p. 67.
Leason et al. (1982), Phytochemistry 21, No. 4, pp. 855–857.
Donn et al. (1984), J. of Mol. & Appl. Genet 2:621–635.
Espin et al. (1982), Mol. Gen. Genet 186:518–524.
Cullimore et al. (1984), J. Mol. & App. Genet 2:589–599.
Young et al. (1983), J. Biol. Chem. 258, No. 8, pp. 11260–11266.
Koziel et al. (1984), J. Mol. & Appl. Genet 2:549–562.
Vasil (1988), Bio/Technology vol. 6:397–402.
Title Page and Table of Contents of the *Journal of Molecular and Applied Genetics*, vol. 2, No. 6 (1984), indicating receipt date of Feb. 15, 1986 by National Library of Medicine.
Newark, P., Nature 305:384–384 (1983).
Sanders, P. G. et al., The EMBO Journal 3(1):65–71.

*Primary Examiner*—Elizabeth C. Weimar
*Assistant Examiner*—Gary Benzion
*Attorney, Agent, or Firm*—Sterne, Kessler, Goldstein & Fox

[57] ABSTRACT

A plant cell which is resistant to a herbicidal glutamine synthetase inhibitor, wherein the resistance is caused by levels of GS activity which, when present in an otherwise herbicidal GS inhibitor sensitive plant cell, render the cell substantially resistant to the herbicidal GS-inhibitor.

24 Claims, 9 Drawing Sheets

THE GLUTAMATE SYNTHASE CYCLE

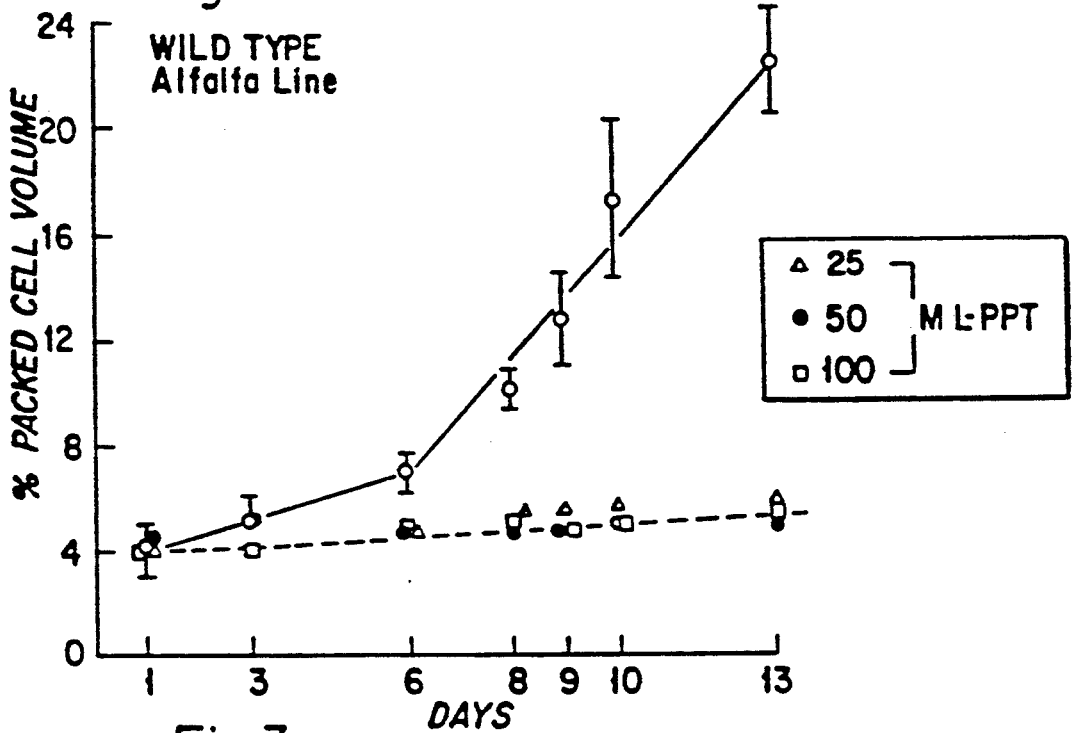
Fig.2 WILD TYPE Alfalfa Line
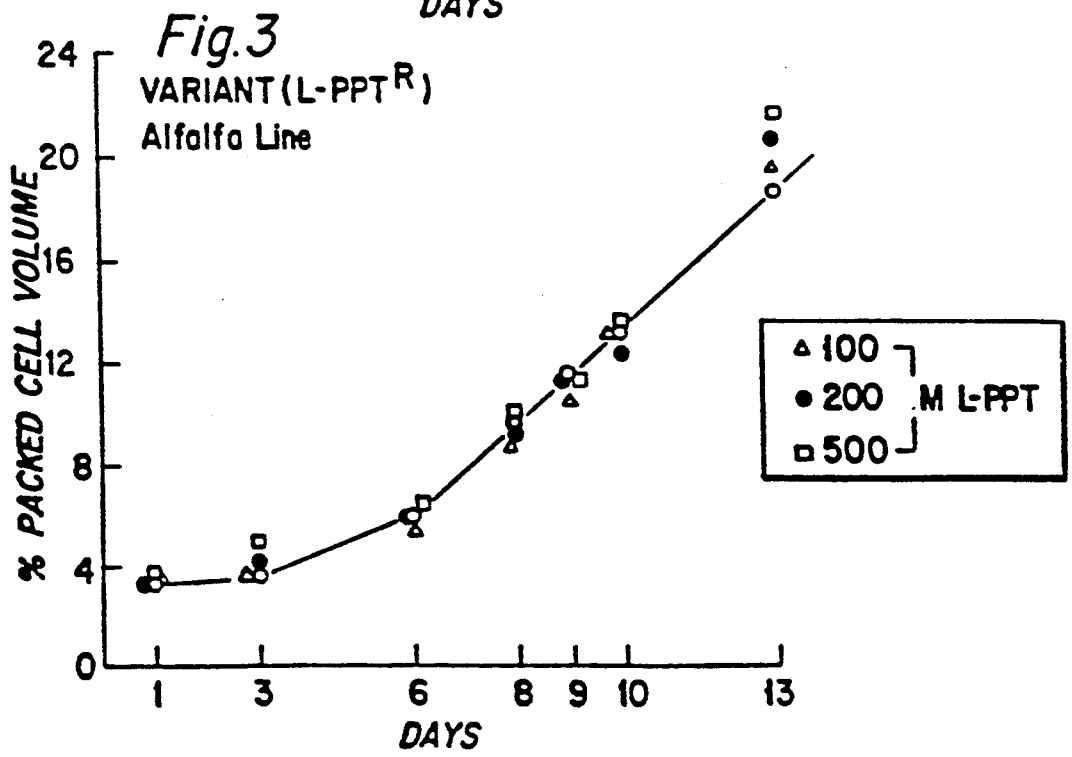
Fig.3 VARIANT (L-PPT$^R$) Alfalfa Line

FIG. 4A

```
                                                                                              Bam HI
    -620  ggatccataatttatatttttttaaaggaataatttactgttttttttaggaaaataatttattgttaacatcaacgaaaa -540  aaccttttaaatatttctcactctgtaatcataaaaaatgagaagtaaacaactagtatttctaaaattgtttaatataattattggaattatatctttaattgtta -432  atcaatcaaataattgaaggaatcctgtgtttttttagtttgtcgtgattaccactaataacaacaataaacaataaaatggaataaaaattagaataattattaatta -324  gagtcgaatttaattgttccaatgaattggtttgactcctaaaataaggatctaacgttttattctctccgttgtcaatttagttgttgactaattcacaaa Acc I
    -216  agtcatgctttgactttaattaaacagggtttcgcaagtgaacggtgagattagacgaatatcgaatttgttttgtaaaaagaatttaattagagtagactagatta -108  tagagaaggagttgtaaccaaaaaaaaagattatagagaaggtgaggaagacagaaaaaaccactaggcTATAAATAAggacccccactgcctcatttctc 1  TATTCACAACAATATTCCGTTTCGTTTCATTGATTCATTGAATCAATCGAATCGAATGAATCTTAGGATTCAATACAGATTCCTTAGATTTTACTAAGTTTGAAAC 109  CAAAACCAAAAAC ATG TCT CTC CTT TCA GAT CTT ATC AAC CTT GAC CTC TCC GAA ACC ACC GAG AAA ATC ATC GCC GAA TAC ATA
                        Met Ser Leu Leu Ser Asp Leu Ile Asn Leu Asp Leu Ser Glu Thr Thr Glu Lys Ile Ile Ala Glu Tyr Ile
```

```
193  TG gttagattcttctctttccctcacatgcttacaaaacagacacataaactcttttttatgatgatgtttgttttgtatgttccgtagtagaa
     Tr
     p 300  aaacactagatttctttctgtctgttttctgcatatgcattaagttacgtccaccgaacgttttttctagaatcattcataatcatcaccatgatatttttttt 408  tattcatgattcatcactataaattaatatcatgagtataataaccagtgattatttttttagttatttttggttatttttcttatatttaa 516  tttattgtttatagatttaagttgatttgggatatgaggatgtttgttttctgtttttttttaggcttaaaccatgatgattttttctgtttttttgatg 624  gttgagtatggtttagtattttactcattctgaaaatgactttgttttttttgtttggaataaaattggaaaaagaagagatttttcagttgtgtctttttgtt 732  gctttgttttcaatcaattttcaatacaaaccaaacctacctgtctaccgcattgtacaatacaaaccaaaccaaaccatgatattaaaactcttgtactaaatat 840  tgtttttttatatcaaaattcaataattaaaatttcccctttttgattaattttttttctcattatgacag G ATT GGT GGA TCT GGT TTG GAC TTG AGG
                                                                                  Ile Gly Gly Ser Gly Leu Asp Leu Arg 937  AGC AAA GCA AGG gtaattaacattctctagctatctaaaaacgaaaaagaaaaaaaaagtgatttttgcttttcattaatttattgataataaa
     Ser Lys Ala Arg 1041 aatgcttttttttttggtgtgcgag         ACT CTA CCA GGA CCA GTT ACT GAC CCT TCA CAG CTT CCC AAG TGG AAC TAT GAT GGT TCC AGC
                                       Thr Leu Pro Gly Pro Val Thr Asp Pro Ser Gln Leu Pro Lys Trp Asn Tyr Asp Gly Ser Ser
```

FIG. 4A(i)

1125 ACA GGT CAA GCT CCT GGA GAA GAT AGT GAA GTT ATT ATC TA gtatgatttttctataatactattattttttaatttttgaatccttaattatg
     Thr Gly Gln Ala Pro Gly Glu Asp Ser Glu Val Ile Ile Ty 1219 taaagatttttgtctttaatttttttttttttttactattttggggttggattccttacag  C CCA CAA GCC ATT TTC AAG GAC CCA
                                                                     r Pro Gln Ala Ile Phe Lys Asp Pro 1315 TTT AGA AGG GGT AAC AAT ATC TTG gtaagtttttttttttttttttaacatatgctggtagtagtcattttcagttcttgaatgtatcaaatggcgtca
     Phe Arg Arg Gly Asn Asn Ile Leu 1415 ttagtccttaaatgtatcaaattactaaaatatctttgaatgtgtcttttttgtcatcaaatttgtcttttgttaatagttgttcttccaatatgttt 1523 tccgttagttagttgatccataaaatcaccaacaaagacacactgatgatgttttaataacttcaatgtattcatgagccatattgacacgcctcacacatttaggg 1631 atcagaatatgacaatcaacttgttatattttgttttaatcatctgtgttcaattcacaacttgactattgtgagtttatgcagctggt 1739 cttgttttcattggtgtaacccctcttttttgtgttttaattcag  GTT ATG TGT GAT GCA TAC ACT CCA GCT GGA GAG CCC ATT CCC ACC
                                                    Val Met Cys Asp Ala Tyr Thr Pro Ala Gly Glu Pro Ile Pro Thr

FIG. 4A(ii)

```
1829  AAC AAG AGA CAT GCA GCT GCC AAG ATT TTC AGC CAT CCT GAT GTT GCT GAA GTA CCA TG gtatcttttgttgctactttgctta
      Asn Lys Arg His Ala Ala Ala Lys Ile Phe Ser His Pro Asp Val Val Ala Glu Val Pro Tr 1916  ttgtaataaccttttttgccacttgttactgtgttctgatcaacaattgttgtatgatttgtgattag    G TAT GGT ATT GAG CAA GAA TAC ACC TTG
                                                                              p Tyr Gly Ile Glu Gln Glu Tyr Thr Leu 2012  TTG CAG AAA GAC ATC AAT TGG CCT CTT GGT GGT TGG CCA GTT GGT GGT TTT CCT GGA CCT CAG gtgaaaactcacaaacatcatcattac
      Leu Gln Lys Asp Ile Asn Trp Pro Leu Gly Trp Pro Val Gly Gly Phe Pro Gly Pro Gln 2100  tgttttttattttatttttcaagctagtactcacttgcacaatcatataagaaaatggtgtgaccatgagtggtaataatgagaaaatgtcccatacctaattgttttta 2208  aatttgtttaaaccatagttttatgtatttttttttatcaaagattcctcaattgaacttgtcttttggtgaatttttattgtcattggttacatctgttctaatt 2316  ttatctgttattaacattgttattttataattgctcaatag    GGA CCA TAC TAT TGT GGA GCT GGT GCT GAC AAG GCA TTT GGC CGT GAC
                                                   Gly Pro Tyr Tyr Cys Gly Ala Gly Ala Asp Lys Ala Phe Gly Arg Asp
```

FIG.4B

```
2406  ATT GTT GAC TCA CAT TAC AAA GCC TGT CTT TAT GCC GGC ATC AAC ATC AGT GGA ATC AAT GGT GAA GTG ATG CCT GGT CAA
      Ile Val Asp Ser His Tyr Lys Ala Cys Leu Tyr Ala Gly Ile Asn Ile Ser Gly Ile Asn Gly Glu Val Met Pro Gly Gln 2487  gtaagttggacttattttaccctttagcattattttactacatttttttcattttaaataaacatatgcttgtgattttttataagttaatctattgttttttta Eco RI
2595  atgtag  TGG GAA TTC CAA GTT GGT CCC TCA GTT GGT ATC TCT GCT GGT GAT GAG ATA TGG GTT GCT CGT TAC ATT TTG GAG
              Trp Glu Phe Gln Val Gly Pro Ser Val Gly Ile Ser Ala Gly Asp Glu Ile Trp Val Ala Arg Tyr Ile Leu Glu 2676  gtaggtggcacatgagtattgactaagtgttattttactatttccaacacctcttttgacttattgaatggaagttagtgttaccttctccaactaactttt 2784  ctttgttatgtgttccaatag AGG ATC ACT GAG GTT GCT GGT GTG CTT TCC TTT GAC CCA AAA CCA ATT AAG gtttgctatttccac
                            Arg Ile Thr Glu Val Ala Gly Val Val Leu Ser Phe Asp Pro Lys Pro Ile Lys 2873  cttttgttttgaatcaagttattctacacaagacatttgtttccaactccttgtctatattgatatactgtctttatattactattaagttgactttgtatttttta 2981  atgcaaaactag GGT GAT TGG AAT GGT GCT GGT GCT CAC ACA AAT TAC AG gtaatgtttgttaattaagtaaatcaaaagactatagttgaat
                   Gly Asp Trp Asn Gly Ala Gly Ala His Thr Asn Tyr Se 3075  attttatatggtcatggttgacaagtgcatccttataatgctgtag C ACC AAG TCT ATG AGA GAA GAT GGT GGC TAT GAA GTC ATC TTG AAA
                                                      r Thr Lys Ser Met Arg Glu Asp Gly Gly Tyr Glu Val Ile Leu Lys
```

FIG. 4B(i)

```
3167  GCA ATT GAG AAG CTT GGG AAG AAG CAC AAG GAG CAC ATT GCT GCT TAT GGA GAA GGC GTT AGA TTG ACA GGG CGA
      Ala Ile Glu Lys Leu Gly Lys Lys His Lys Glu His Ile Ala Ala Tyr Gly Glu Gly Asn Glu Arg Arg Leu Thr Gly Arg

3248  CAT GAG ACA GCT GAC ATT AAC ACC TTC TTA TGG gtaagcaaataataatattgttcttctctgaagataaaaagtttcatctgacattaattttgt
      His Glu Thr Ala Asp Ile Asn Thr Phe Leu Trp 3345  tccgatttcaagtctactacatatggggttagtccggttggggacttgacctagtctgaaccatttgttttttgttgttgttctaattgttggcgtggcttgtgttatt 3453  tgaag      GGT GTT GCA AAC CGT GGT GCG TCG ATT AGA GTT GGA AGG GAC ACA GAG AAA GCA GGG AAA GGT TAT TTC GAG GAT
                 Gly Val Ala Asn Arg Gly Ala Ser Ile Arg Val Gly Arg Asp Thr Glu Lys Ala Gly Lys Gly Tyr Phe Glu Asp BamHI
3533  AGG AGG CCA TCA TCT AAC ATG GAT CCA TAT GTT GTT ACT TCC ATG ATT GCA GAC ACC ATT CTC TGG AAA CCA TAA GCCA
      Arg Arg Pro Ser Ser Asn Met Asp Pro Tyr Val Val Thr Ser Met Ile Ala Asp Thr Thr Ile Leu Trp Lys Pro End 3615  CCACACACACATGCATTGAAGTATTGAAAGTCATTGTTGATTCCGCATTAGAATTGGTCATTGTTTTTCTAGGATTGGATTTGTGTTATTGTTATGGTTCACAC StuI
3723  TTTGTTTGTTGAATTTGAGGCCTTGTTATAGGTTTCATATTTCTTTCTCTTGTTCTAAGTAAATGTCAGAATAATAATGTAATATTTGTCCGTAAAA taattattg 3830  ttgattatgttttatt
```

FIG. 4B(ii)

PLANT CELLS RESISTANT TO HERBICIDAL GLUTAMINE SYNTHETASE INHIBITORS

CROSS REFERENCE TO RELATED APPLICATION

The application is a continuation of application Ser. No. 07/399,420, filed Aug. 28, 1989, now abandoned, which is a continuation-in-part of application Ser. No. 081,455, filed in the U.S. Patent and Trademark Office on Aug. 4, 1987, now abandoned, which is a continuation-in-part of application Ser. No. 833,156, filed in the U.S. Patent and Trademark Office on Feb. 27, 1986, now abandoned which is a continuation-in-part of application Ser. No. 742,846, filed in the U.S. Patent and Trademark Office on Jun. 10, 1985, now abandoned, which is a continuation-in-part of application Ser. No. 656,488 filed in the U.S. Patent and Trademark Office on Oct. 1, 1984, now abandoned.

FIELD OF THE INVENTION

The present invention relates to the use of recombinant DNA technology for the transformation of plant cells and, more specifically, the design and construction of plant cells which are resistant to herbicidal plant glutamine synthetase inhibitors, such as phosphinothricin.

BRIEF DESCRIPTION OF THE BACKGROUND ART

Glutamine Synthetase (GS) is a plant enzyme which has a central role in the assimilation of ammonia and in the regulation of nitrogen metabolism. Since in most plants glutamine synthetase is, via the glutamine synthetase/glutamate synthase pathway (FIG. 1), the only efficient way to detoxify ammonia released by nitrate reduction, amino acid degradation or photorespiration, plants are very susceptible to potent inhibitors of glutamine synthetase.

One of the most potent glutamine synthetase inhibitors known at present is phosphinothricin (1) (hereinafter PPT):

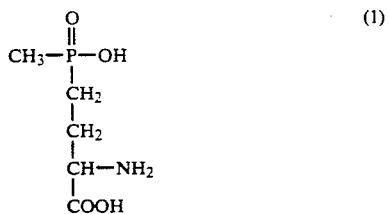

PPT is a glutamic acid analogue. The compound was initially isolated from a tripeptide antibiotic produced by *Streptomyces viridochromogenes* (Bayer, E., et al., *Helvetica Chimica Acta* 55:224 (1972), see also German Patent DOS 2717440, Hoechst, A.G.). PPT is a potent competitive inhibitor of glutamine synthetase from *E. coli* with a $K_i$ of 0.0059 mM.

Schwerdtle, F. (*Zeitschrift fur Pflanzen-Krankheiten und Pflanzenschutz*, IX:431–440 (1981)) demonstrated that PPT is a non-selective foliar herbicide for the control of undesirable mono and dicotyledonous plants in orchards, vineyards, plantations with minimum tillage, direct drilling, and as a harvest aid. Field trials in West Germany, Spain, South Africa, U.S.A. and Japan showed that most dicotyledonous weeds were well controlled. For monocotyledonous weeds somewhat higher quantities were needed for good control. Leason, M., et al. (*Phytochemistry* 21:855–857 (1982)) demonstrated that PPT is a mixed competitive inhibitor of pea leaf glutamine synthetase with an apparent $K_i$ value of 0.073 mM.

It would be of great interest to be able to confer resistance to PPT, as well as to other GS inhibitors to selected plans, since herbicidal selectivity is quite crucial in any commercially useful herbicide. PPT, as indicated, is non-selective.

There is some precedent for the existence of glutamine synthetases resistant to other compounds. It is known that methionine sulfoximine (MSO), another glutamate analogue, is a mixed competitive inhibitor ($K_i$ value of 0.16 mM) of pea leaf glutamine synthetase (Leason, M., et al., *Phytochemistry* 21:855–857 (1982)). Miller, E. S. and Brenchley, J. E. (*The Journal of Biological Chemistry* 256:11307–11321 (1981)) studied the properties of several mutants of Salmonella resistant to MSO. One mutation apparently altered glutamine synthetase at the ammonia binding domain, conferring MSO resistance. More recent, Young and Ringold (ibid 258:11260–11266 (1983)) have reported that mouse 3T6 cells grown in the presence of MSO developed resistance thereto. MSO resistant cells had mRNA enriched for glutamine synthetase, and the authors suggested that this observation implied an amplification of the gene. See also Sanders and Wilson, *EMBO. J.* 3:65–71 (1984). Neither the Miller, Young, nor Sanders studies were reported on plant GS.

Further, prior to the present invention no studies have been reported on attempts to confer resistance to herbicidal GS inhibitors, such as PPT, by manipulating the glutamine synthetase genes in plant cells.

It would therefore be desirable to develop plant cells which are resistant to herbicidal inhibitors of GS, such as PPT, by manipulating the plant glutamine synthetase genes in said cells. In such manner, it would be possible to confer herbicidal selectivity to any given plant.

SUMMARY OF THE INVENTION

The present invention arose out of the discovery that resistance to PPT in plants can arise due to overproduction of glutamine synthetase, a phenomenon which, in the initial experiments, was shown to be due to an underlying gene amplification mechanism. Upon applying selective pressure on certain plant cells in tissue culture, it was possible to isolate PPT resistant strains. The resistance, however, was not due to the presence of a structural mutant of glutamine synthetase which had less affinity for PPT, but rather, due to gene amplification and concomitant increased concentrations of the enzyme in the plant cells. Out of these initial observations arose the concept of the invention of developing plant cells which overproduce glutamine synthetase (and thus show herbicidal GS-inhibitor resistance), either by gene amplification or by other, different, mechanisms than gene amplification.

The invention is therefore based on producing a plant cell which is resistant to a herbicidal glutamine synthetase (GS) inhibitor, wherein said resistance is caused by plant cell levels of GS activity which, when present in an otherwise herbicidal GS-inhibitor sensitive plant cell, render said cell substantially resistant to said herbicidal GS inhibitor.

The invention can be accomplished by a variety of methods and thus encompasses various embodiments.

For example, in one embodiment, the invention is based on producing a plant cell carrying a gene combination comprising:

A) a first genetic sequence coding for a glutamine synthetase (GS) functional in said plant cell, operably linked to B) a second genetic sequence capable of increasing the levels of expression of said first genetic sequence such that when said combination is present in an otherwise herbicidal GS-inhibitor sensitive plant cell, said cell is substantially resistant to said herbicidal GS-inhibitor.

The invention also comprises a gene combination as described, present in the genome or in a replicating extrachromosomal element of a plant species, which species is heterologous for said first or second genetic sequence or for both.

In another embodiment, the invention is based on producing a herbicidal GS-inhibitor resistant plant cell which contains significantly increased levels of GS activity by virtue of having a significantly larger number of copies of the wild GS gene than the corresponding herbicidal GS-inhibitor sensitive plant cell. In this embodiment, a plant can be obtained by inducing GS gene amplification by selective pressure in cell culture to obtain a resistant variant or strain, followed by growth and development thereof into a callus and full grown plant, and sexual reproduction thereof. Alternatively, a plant can be obtained by inducing GS gene amplification by selection in cell culture of a resistant donor variant or strain, followed by protoplast fusion of the donor cells with an appropriate acceptor cell to yield a morphogenetic hybrid capable of further growth and development.

As another alternative, a resistant plant cell which contains a significantly larger number of copies of the wild gene than the corresponding sensitive cell can be obtained by introducing multiple expressible copies of the wild GS gene into an appropriate extra-chromosomal element capable of replication, or into the genome of the plant cell itself. This can be accomplished by transformation at the cell culture stage or at the whole plant stage. Stable multicopy organelles carrying the GS wild gene can also be used to introduce significantly larger numbers of the GS gene into a cell.

The invention further comprises herbicidal GS inhibitor-resistant, transformed plant cells per se, which in their otherwise untransformed state would be herbicidal GS inhibitor sensitive. Whole plants which are herbicidal GS inhibitor resistant are also included.

The invention also comprises intermediate vehicles capable of serving as transformation vectors for plant cells carrying genetic information as described, capable of conferring herbicidal GS inhibitor-resistance, and method of conferring resistance to plant cells.

The invention further comprises a method of plant control achieved by contacting herbicidal GS inhibitor sensitive plants with plant controlling amounts of a herbicidal GS inhibitor, while in the presence of, and simultaneously contacting plants made resistant to said inhibitor by the methods described.

DESCRIPTION OF THE FIGURES

The invention will be better understood by reference to the accompanying Figures where

FIG. 2 shows the growth characteristics of a wild type (PPT-sensitive) alfalfa cell line in the absence (o) and in the presence of 25 (Δ), 50 ( ) and 100 (□) μm L-PPT.

FIG. 3 shows the growth characteristics of a variant PPT resistant alfalfa cell line in the absence (o) and in the presence of 100 (Δ), 200 ( ) and 500 (□) μm L-PPT.

FIGS. 4A, 4A(i), 4A(ii), 4B, 4B(i), 4B(ii) show the complete functional sequence for glutamine synthetase.

DEFINITIONS

Figure 1:
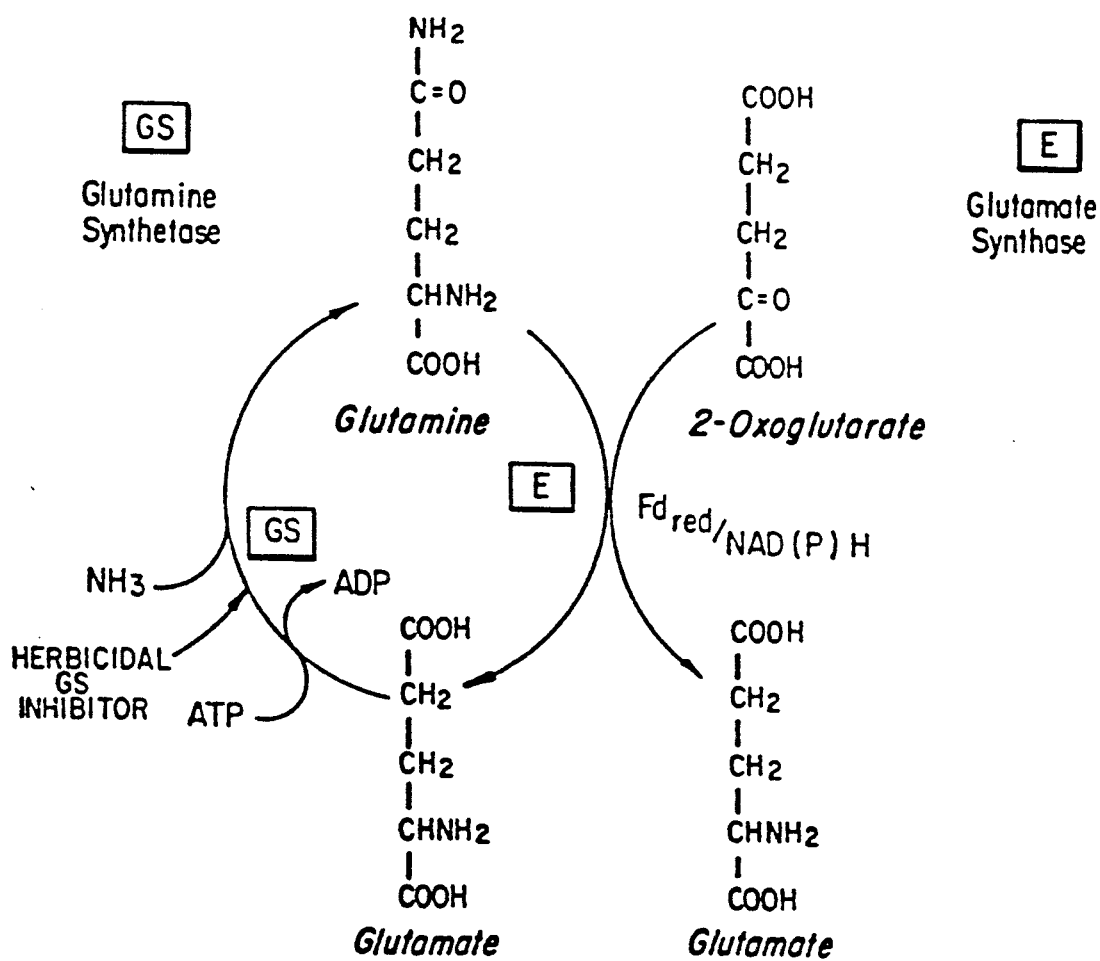
FIG. 1 shows the glutamine synthetase/glutamate synthase cycle, wherein it is shown that GS catalyzes the formation of glutamine from glutamic acid and ammonia in a reaction driven by the hydrolysis of ATP to ADP and inorganic phosphate. The amide nitrogen of glutamine provides the source of nitrogen for many biosynthetic reactions, indicating a central role for GS in nitrogen metabolism. The herbicidal GS inhibitor, by inhibiting GS, prevents the biosynthesis of glutamine, thereby preventing ammonia detoxification.

In the description that follows, a number of terms used in recombinant DNA, plant genetics technology and in the present invention are extensively utilized. In order to provide a clear and consistent understanding of the specification and claims, including the scope to be given such terms, the following definitions are provided:

Nucleotide. A monomeric unit of DNA or RNA consisting of a sugar moiety, a phosphate, and a nitrogenous heterocyclic base. The base is linked to the sugar moiety via the glycosidic carbon (1' carbon of the pentose). The combination of a base and a sugar is called a nucleoside. Each nucleotide is characterized by its base. The four DNA bases are adenine (A), guanine (G), cytosine (C) and thymine (T). The four RNA bases are A, G, C and uracil (U).

Genetic sequence. A linear array of nucleotides connected one to the other by phosphodiester bonds between the 3' and 5' carbons of adjacent pentoses.

Functional Genetic Sequence. A genetic sequence coding for a polypeptide having desired activity, regardless of whether the sequence is shorter or longer than that of the full length sequence for the polypeptide. It is also referred to as "functional gene."

Codon or Triplet. A DNA sequence of three nucleotides which encodes through mRNA an amino acid, a translation start signal or a translation termination signal. For example, Codons TTA, TTG, CTT, CTC, CTA and CTG encode for the amino acid leucine. TAG, TAA, and TGA are translation stop signals, and ATG is a translation start signal.

Reading frame. The grouping of codons during translation of mRNA into an amino acid sequence. During translation, the proper reading frame must be maintained. For example, the sequence GCTGGTTGTAAG may be translated into three reading frames or phrases depending on whether one starts with G, with C, or with T, and thus may yield three different peptide products.

Two sequences are in operable linkage when the reading frame of one sequence is linked to the other so that both operate in combination as if they would be present independently.

Transcription. The process of producing mRNA from a functional gene.

Translation. The process of producing a polypeptide from mRNA.

Expression. The process, starting with a functional gene, to produce its polypeptide, being a combination of transcription and translation.

Cloning vehicle. A plasmid, phage DNA, or other DNA sequences which are able to replicate in a host cell, which are characterized by one or a small number of endonuclease recognition sites at which such DNA sequences may be cut in a determinable fashion without loss of an essential biological function of the DNA, and which contain a marker suitable for use in the identification of transformed cells. A typical example is an antibiotic resistance marker. The word "vector" is sometimes used for a cloning vehicle.

Expression vehicle. A vehicle, analogous to a cloning vehicle, which is particularly useful for production in host cells of a polypeptide by expression of the functional gene coding for said polypeptide, present in the vehicle.

Replication vehicle. A cloning or expression vehicle.

Phage or bacteriophage. A bacterial virus which may consist of DNA sequences encapsulated in a protein envelope or coat.

Plasmid. A non-chromosomal double stranded DNA sequence comprising an intact "replicon," such that the plasmid is replicated in or incorporated into the genome of a host cell. When the plasmid is placed within a unicellular or multicellular organism, the characteristics of that organism may be changed or transformed as a result of the DNA of the plasmid. For example, a plasmid carrying the gene for kanamycin resistance transforms a cell previously sensitive to kanamycin into one which is resistant to it.

Cloning. The process of obtaining a population of organisms or DNA sequences derived from one such organism or sequence by asexual reproduction.

Expression control sequences. A genetic sequence that controls and regulates expression of functional genetic sequences when operably linked to those sequences. They include sequences known to control the regions which regulate that expression. They comprise both promoter and terminator sequences.

Plant Promoter. An expression control sequence which is capable of causing the expression in said plant of any homologous or heterologous genetic sequences or sequences operably linked to such promoter.

Overproducing Plant Promoter (OPP). A plant promoter capable of causing the expression in a transformed plant cell of any operably linked functional genetic sequence or sequences to levels (measured by mRNA or polypeptide quantities) which are substantially higher than the levels naturally observable in host cells not transformed with said OPP.

Degeneracy. An informational property according to which each amino acid in nature can be coded by more than one codon. For example, leucine can be coded by TTg, TTA, CTA, CTT, CTC or CTG.

By degenerate variations as used in the present application and claims, is meant any variation of the polynucleotide fragments of the invention due to the degeneracy of the genetic code. For example, as long as the resulting material still codes for functional GS, or portions thereof, such material is designed to be included in the present invention.

Glutamine Synthetase (GS). The definition of this enzyme is functional, and includes any glutamine synthetase capable of functioning in a given desired plant to transform glutamic acid to glutamine in the GS cycle. The term therefore includes not only the enzyme from the specific plant species involved in the genetic transformation, but may include GS from other plant species or microbes or even other eukaryotes, if such GS is capable of functioning in the transformed plant cells. The terms include proteins or polypeptides having more or less than the total structural length of natural plant GS, such as functional partial fragments of GS, or their analogues.

Phosphinothricin (PPT). The compound of formula (1), supra, in its biologically active form. It may be the L-, or D- or D,L- forms, and may be alone or in combination with other inert or active compounds which do not interfere with PPT activity.

DESCRIPTION OF THE PREFERRED EMBODIMENTS PRODUCTS

The invention comprises at its most fundamental level a plant cell which is resistant to a herbicidal glutamine synthetase inhibitor wherein the resistance is caused by levels of GS activity which, when present in an otherwise herbicidal GS inhibitor-sensitive plant cell, render the cell substantially resistant to the herbicidal GS inhibitor.

The terms "herbicidal glutamine synthetase inhibitor" are meant to include any inhibitor, competitive or noncompetitive, that significantly decreases the glutamine synthetase activity of a plant cell of a given species and, as a consequence thereof, causes herbicidal effects in the plant cell. The herbicide resistant plant cell or whole plant survives without irreversible damage a herbicidal GS inhibitor concentration which is lethal for wild type individuals of the same species. Normally, a five-fold or higher increase in herbicidal GS inhibitor resistance is considered significant. However, this number varies from plant species to plant species, and from herbicide to herbicide. It is therefore not feasible to provide a single level for all of the several plant species and herbicides covered by the present invention. Such level, however, can be readily ascertained by those skilled in the art.

Among the herbicidal GS inhibitors covered by the invention are phosphinothricin, methionine sulfoximine, as well as other glutamic acid analogues.

The glutamine synthetase may or may not be from the specific plant cell being transformed. All that is necessary is that the genetic sequence for the enzyme be expressed, and produce, a functional enzyme in the final plant cell. Thus, the invention comprises plant cells containing either homologous GS genes or heterologous GS genes (and their respective expression products). Broadly, the enzyme might also be that of other plant species, or even enzymes from different organisms, such as microorganisms or animals. Preferred are plant glutamine synthetase genes and their expression products. Of particular interest are glutamine synthetase genes from the particular plant species which serves as the host in the genetic manipulation, i.e., homologous GS genes. One such glutamine synthetase gene utilizable in the rDNA molecules of the invention is illustrated in Example 2.

Any plant cell which is sensitive to herbicidal GS inhibitors, which is capable of undergoing genetic manipulation by the genetic constructs or methods of the invention, and is capable of expressing said constructs, can be used in the present invention. Among dicotyledonous plants are included various species of potato (*Solanum tuberosum*); tomato (*Lycopersicon esculentum*); pepper (*Casicum annumm*); tobacco (*Nicotiana tabacum*); various species of Brassica, especially rapeseed (*Brassica napus*), various legumes, for example alfalfa (*Medicago sativa*), clover (Trifolium spec.), soybean (*Glycine max*), groundnut (*Arachis hypogaea*), various species of beans (Phaseolus spec., Vicia spec., Vigna spec.), peas (*Pisum sativum*), root crops as beets (*Beta vulgaris*), carrots (*Daucus carota*) and sweet potatoes (*Ipomoea batatus*).

There are a variety of embodiments encompassed in the broad concept of the invention. The herbicidal GS-inhibitor resistant plant cell can contain significantly higher levels of GS activity by any of a variety of mechanisms and/or genetic constructs.

For example, the invention comprises, in one of its embodiments, a combination of two genetic sequences: (a) a first genetic sequence coding for a glutamine synthetase functional in a given plant cell, operably linked downstream from (b) a second genetic sequence capable of increasing the levels of gene product of said first sequence such that when the combination is present in an otherwise herbicidal GS-inhibitor sensitive plant cell, said cell is substantially resistant to said herbicidal GS-inhibitor.

The second genetic sequence may be a promoter or an enhancer sequence. If a promoter, it may be a GS promoter or a promoter of another structural gene. In either of the latter two events, the promoter useful in the combination is an overproducing plant promoter. The only essential characteristic of such promoter is that, when in operable linkage with the genetic sequence for glutamine synthetase, it be capable of promoting expression of said glutamine synthetase to levels such that when the combination is present in an otherwise herbicidal GS-inhibitor sensitive plant cell, the cell is substantially resistant to said GS-inhibitor. Thus, the choice of what plant promoter to use is ruled by functional considerations. The plant promoter will be heterologous or homologous to the host cell. The native, endogenous promoter of said host cell would be incapable of causing resistance by overproduction of GS, since such native promoter normally promotes expression of GS to levels which are so low as to be substantially or completely inhibited by normally used plant-controlling herbicide concentrations. Thus, under one embodiment of the present invention, the native promoter is replaced by an OPP.

Among useful OPPs are included the promoter of the small subunit (ss) of the ribulose bi-phosphate carboxylase, and of the chlorophyll a/b binding protein. The expression of these two genes has been shown to be light induced at the transcriptional level in green tissue (see, for example, *Genetic Engineering of Plants. An Agricultural Perspective*, A. Cashmore, Plenum, New York, 1983, pages 29-38, Coruzzi, G., et al., *The Journal of Biological Chemistry* 258:1399 (1983), or Dunsmuir, P., et al., *Journal of Molecular and Applied Genetics* 2:285 (1983)).

The invention extends to any plant cell modified according to the methods described, or modified by any other methods which yield herbicidal GS-inhibitor resistance. The plant cell may be alive or not, by itself, in tissue culture or as part of a multicellular plant or a part thereof. Such a multicellular plant, which in its untransformed state is herbicidal GS-inhibitor sensitive, would be resistant when its cells are resistant according to the invention.

Parts obtained from the plant, such as flowers, seeds, leaves, branches, fruit and the like are also covered by the invention, as long as these parts comprise herbicidal GS-inhibitor resistant cells, as noted. In particular, plant parts may be alive or not. Thus, a genetically modified tomato, carrot or tobacco leaf obtained from a resistant tomato, carrot or tobacco plant is included in the invention, even if separate from the plant of origin.

PROCESSES OF PRODUCTION AND INTERMEDIATES USED THEREIN

Various methodologies are applicable to carry out the different embodiments of the invention. For example, if the herbicidal GS-inhibitor resistance is brought about by providing significantly increased copies of a structural GS gene (as opposed to the previously mentioned overproduction of the wild gene), available methodologies include selection for a cell which is resistant by virtue of GS gene amplification, or, alternatively, introduction of multiple copies of the GS gene into the genome or into a replicating extrachromosomal element.

Selection is carried out in an appropriate culture medium by cultivating plant cells in the presence of stepwise increases of the herbicidal GS-inhibitor in the medium. After a given period of time has elapsed, such as, for example, a few weeks to several months, it is possible to select a cell population which is several-fold more resistant to the herbicidal GS-inhibitor than the original plant cells. For example, when the cells are alfalfa and the inhibitor is PPT, it has been possible to obtain a PPT-resistant alfalfa cell line after one year of stepwise PPT increases, which line was twenty-fold more resistant to PPT than the original line. When the resistant line was subcultured for several months in the absence of the inhibitor, a slow decline in the percentage of resistant cells was observed in plating experiments on inhibitor-containing agar media, but after more than six months it was still possible to reselect highly resistant cell clones. This was never possible by plating wild-type cells.

Regeneration of calli and grown plant from tissue culture cells is known to those skilled in the art, and it varies from species to species. See, for example, Sheperd, *Scientific American*. 1982, herein incorporated by reference. Generally, a suspension of protoplasts containing multiple copies of the GS gene or containing the genetic sequence combination is first provided. Embryo formation can then be induced from the protoplast suspensions, to the stage of ripening and germination as natural embryos. The culture media will generally contain various amino acids, and hormones such as auxin and cytokinins. It is advantageous to add glutamic acid and proline to the medium, especially for such species as corn and alfalfa. Shoots and roots normally develop simultaneously. Efficient regeneration will depend on the medium, on the genotype, and on the history of the culture. If these three variables are controlled, then regeneration is fully reproducible and repeatable.

For the genotypes of some species, such as tobacco, alfalfa, potato, tomato, petunias, soy beans, rapeseed, and some fruit trees and carrots, regeneration has been clearly demonstrated in the prior art. Such regeneration is well within the skill of the art if the appropriate genotype and history is chosen by screening. Generally, after about more than one year of subculturing, the efficiency of plant regeneration decreases from a given cell culture. Therefore, regeneration is normally most successful if it is initiated shortly after the provision of an appropriate resistant cell culture.

Alternatively, and especially useful in cell cultures which are older than several months or one year, the amplified GS gene can be carried into regenerative system by crossing and/or fusion. See, for example, Cocking et al, *Nature* 293:265 (1981) herein incorporated by reference. In this method, a herbicidal GS-inhibitor resistant cell line is provided by selection, and a culture suspension of rapidly dividing cells is obtained by methods well known to those of skill in the art. Protoplasts are isolated therefrom, and preferably irradiated with an amount of radiation and for a time sufficient to inactivate, if not completely irreversibly damage, the host cells. For example, x-ray radiation of 20 Krads can be used advantageously. After irradiating the donor protoplasts, the same are fused with acceptor protoplasts from appropriate susceptible cells. Various methods exist to obtain fusions, such as, for example, polyethylene glycol fusion, high calcium treatment, combinations of both, or even recently, electrofusion. After fusion has occurred, selective growth of the fusion product can be carried out since the fusion product should be herbicidal GS-inhibitor resistant. In particular, if a donor is used which is no longer morphogenetic (i.e., the history of the donor culture is such that several months or upwards of a year may have already elapsed since the original selection), then a simple selection in herbicidal GS-inhibitor containing media can be carried out.

Another method of introducing genetic material into plant cells is to infect a wounded leaf of the plant with transformed *A. tumefaciens* bacteria. Under appropriate growth conditions a ring of calli forms around the wound. The calli are then transferred to growth medium, allowed to form shoots, roots and develop further into plants. Alternatively, grafting onto whole plants can also be done.

An alternative method to introduce multiple copies of the GS gene into the plant cell is by self-ligating a copy of a functional GS (genomic or cDNA) structural gene, utilizing methods well known to those of skill in recombinant DNA technology. The structural genes, each containing its individual promoter, are operably linked to each other by means of appropriate linkers, and 10–30 copies of each gene can in certain instances be introduced into an appropriate replicable expression vehicle, such as a Ti plasmid. Alternatively, the genetic material can be micro-injected directly into plant embryo cells. In the case of monocotyledonous plant, pollen may be transformed with total DNA or an appropriate functional clone providing resistance, and the pollen then utilized to produce progeny by sexual reproduction.

Of course, any other methods utilizable to increase GS activity in a given cell to such levels as will make the cell herbicidal GS-inhibitor resistant can be utilized. Of particular interest in this invention is the operable linkage of a genetic sequence coding for a structural GS gene to another genetic sequence capable of overproduction of the gene product derived therefrom. This linkage of genetic sequences can be introduced into appropriate plant cells, for example, by means of the Ti plasmid.

The introduction of genetic material into plant cells, especially by use of the so-called tumor inducing (Ti) plasmid of *Agrobacterium tumefaciens*, is a reproducible and predictable technology. (See, for example, Caplan, A., et al., "Introduction of Genetic Material into Plant Cells," *Science:*815–821 (November, 1983); Schell, J. and Van Montagu, M., "The Ti Plasmid as Natural and as Practical Gene Vector for Plants," *Bio/Technology:* April 1983, pps. 175–180; Horsch et al., "Inheritance of Functional Foreign Genes in Plants," *Science* 233:496–498 (1984); Fraley, R. T., et al., *Proc. Nat. Acad. Sci. USA* 80:4803 (1983), Watson et al., *Recombinant DNA. A Short Course,* Scientific American Books, 1983, pp. 164–173; and Old and Primrose, *Principles of Gene Manipulation,* 2d Ed., U. Cal. Press, 1981, pp. 138–156, herein being incorporated by reference.

Ti plasmids contain two regions essential for the production of transformed cells. One of these, named transfer DNA (T DNA), induces tumor formation. The other, termed virulent region, is essential for the formation but not maintenance of tumors. Transfer DNA, which transfers to the plant genome, can be increased in size by the insertion of the multiply linked GS genes or of the gene combination of the invention without its transferring ability being affected. By removing the tumor causing genes so that they no longer interfere, the modified Ti plasmid can then be used as a vector for the transfer of the gene constructs of the invention into an appropriate plant cell. The foreign DNA to be inserted is usually introduced between the terminal sequences flanking the T-region.

A particularly useful Ti plasmid vector is pGV3850, a non-oncogenic derivative of the nopaline Ti plasmid C58. (See Caplan et al., supra.) This vector utilizes the natural transfer properties of the Ti plasmid. The internal T-DNA genes that determine the undifferentiated crown gall phenotype have been deleted and are replaced by any commonly used cloning vehicle (such as pBR 322). The cloning vehicle sequence contained between T-DNA border regions serves as a region of homology for recombination to reintroduce foreign DNA cloned in a derivative of the same cloning vehicle. Any gene construct of the invention cloned in such plasmid can thus be inserted into pGV 3850 by a single recombination of the homologous sequences. Antibiotic resistance markers can be added to the plasmid to select for the recombination event. Herbicide resistance can of course be also used concomitantly or independently. The presence of the nopaline synthase (nos) gene in this vector makes it easy to monitor the efficiency of transformation using pGV 3850. A callus in tissue culture can then be tested for the presence of nopaline.

After transformation of the plant cell or plant, the same may be selected by aid of an appropriate marker, such as antibiotic resistance, or more relevant, herbicide resistance, and then grown in conventional ways. In tobacco, protoplast cultures three to five days after the protoplast isolation are suitable for the transformation by Agrobacteria harboring the appropriate Ti-plasmid which contains in its T-DNA region the hybrid GS-gene described. After two days of cocultivation of the protoblast borne cells and the Agrobacteria, the plant cells can be washed by centrifugation and resuspended on fresh medium several times. This removes most of the bacteria. The remaining bacteria are killed by a suitable antibiotic, for example, cefotaxime (400–1,000 $\mu$g/ml), added to the protoplast culture medium. The cells are cultivated on nonselective media until they form visible cell aggregates (calli). Then they are plated on media containing the proper herbicide concentration which kills all wild type cells. Only the transformants which express the incorporated GS-hybrid gene survive and continue to grow. These calli can be easily induced to regenerate shoots when transferred to Maraschige and Shoog-medium containing 1 mg/l 6-benzyladenine and 0.1 mg/l naphthalene acetic acid. The shoots can be rooted on hormone free MS-medium or directly on perlite or vermiculite, and transferred to pots. The plantlets are ready to grow in the greenhouse and can be tested for herbicide resistance.

Other systems, such as cauliflower mosaic virus, CaMV (Hohn, B., et al., in "Molecular Biology of Plant Tumors," *Academic Press*, New York 1982, pps. 549–560; and Howell, U.S. Pat. No. 4,407,956) can also be used. The entire CaMV viral DNA genome is inserted into a parent bacterial plasmid creating a recombinant DNA molecule which can be propagated in bacteria. After cloning, the recombinant plasmid is cleaved with restriction enzymes either at random or at unique sites in the viral portion of the recombinant plasmid for insertion of the gene combination of the invention. A small oligonucleotide, described as a linker, having a unique restriction site may also be inserted. The modified recombinant plasmid again may be cloned and further modified by introduction of larger pieces of a gene construct into the unique restriction site of the linker. The modified viral portion of the recombinant plasmid is then excised from the parent bacterial plasmid, and used to inoculate the plant cells or plants. This virus is described in the aforementioned Howell patent as being particularly good for insertion of genes capable of enhanced production of protein, greater tolerance to stress, resistance to pests and pesticides, nitrogen fixation, and the like.

Normally, the desired GS sequences are operably linked in vitro to each other or to an overproducing promoter, by known recombinant methodology. For example, the structural gene for GS, normally the genomic version thereof, is separated from its normal promoter by restriction on the region between such promoter and the initiation AUG codon. A transcriptional fusion with, e.g., the small subunit of the ribulose biphosphate carboxylase is then carried out. The construct is then inserted into an appropriate restriction site of the plant vehicle.

For example, when using CaMV DNA as a vehicle, the genetic construct is inserted into a site or sites in the viral DNA, without destroying infectivity of the viral DNA or its movement throughout the plant. Thus, the construct can be inserted into a variety of restriction sites, cloning the product and determining whether the essential characteristics of the virus have been retained. In this manner, one can rapidly isolate a relatively large amount of modified virus which can be screened for infectivity and movement. After the viral portion of the hybrid DNA plasmid has been modified, the modified virus may be excised from the hybrid DNA plasmid, and may be used to inoculate plants directly in linear form or ligated in circles.

Various techniques may be employed for infecting plant cells with CaMV vehicles. Young leaves may be mildly abraded and then contacted with the viral DNA. After infection, the viral DNA may be transmitted by aphids, where the aphid transmissible gene is operative. Mechanical techniques can also be employed. Alternatively, tissues or single cells may be infected.

USES

The use of vehicles containing the gene constructs of the invention is as intermediates in the preparation of whole herbicide-resistant plants cells and plants. Thus, not only the plant cells made resistant according to the methods of the invention, but also all of the vehicles or vectors, derive their utility from the utility of the final product, the whole plant.

The utility for a whole plant made herbicide resistant according to the invention is obvious. Such a plant, when brought into contact with otherwise plant controlling or suppressing amounts of herbicide, would be resistant thereto. This would allow herbicide treatment to be selective for any desired plant or group of plants.

In addition, the resistance to herbicide would enable its use as a selectable marker in the transfer of other genes to the plant, or cells thereof.

By the terms "plant controlling amounts of herbicidal GS-inhibitor" is meant to include functionally, an amount of herbicide which is capable of affecting the growth or development of a given plant. Thus, the amount may be small enough to simply retard or suppress the growth or development, or the amount may be large enough to irreversibly destroy the sensitive plant. Normally, most dicotyledonous plants and weeds may be controlled at rates of between 0.5 to 1.5 kg/ha ai. For monocotyledonous plants, rates between 0.5 kg/ha ai, and up to about 2.0 kg/ha ai are normally used. The herbicide can, of course, be contacted with the appropriate plant using well known spraying or spreading methods. For example, foliar administration used in the prior art for control of weeds by PPT can be used with PPT-resistant plants falling within the invention.

The invention also encompasses a method of plant control which comprises contacting a herbicidal GS-inhibitor sensitive plant cell or plant, with plant controlling amounts of herbicidal GS-inhibitor, wherein the contact is carried out while the sensitive plant cell or plant is present simultaneously with or among the herbicidal GS-inhibitor resistant plant cells or plants of the invention. Thus, foliar herbicidal treatment of plants in a field or cultivar, which plants include both those comprising herbicide resistant plant cells and those comprising herbicide sensitive plant cells, and wherein both are simultaneously contacted with the herbicidal GS-inhibitor during the treatment operation, is a method included in the present invention.

Having now generally described this invention, the same will become better understood by reference to certain specific examples which are included herein for purposes of illustration only and are not intended to be limiting unless otherwise specified.

EXAMPLE 1

Isolation and Characterization of PPT-Resistant Alfalfa Cell Culture

An alfalfa cell line which is able to grow in the presence of 3 mM L-phosphinothricin in the culture medium was selected. Alfalfa was chosen since it is one of the model plants in which the regeneration of a whole plant from single isolated cells or protoplasts can be readily achieved.

The selection of the phosphinothricin resistant alfalfa line was done by stepwise increase of the inhibitor concentration in the liquid culture medium. Within 6 months a cell population was selected which was at least 20-fold more resistant to phosphinothricin than the original cell line. Measuring the packed cell volume of the suspension cultures revealed that wild type cells were completely inhibited by $2.5 \times 10^{-5}$M L-phosphinothricin. The resistant cells grew as well in the presence of $5 \times 10^{-4}$M of the compound as in its absence (FIGS. 2 and 3).

When the protein patterns of crude cell extracts of the susceptible and resistant cell lines were compared by SDS-polyacrylamide gel electrophoresis, the overproduction of a polypeptide in the molecular weight range 40–42 KD could be observed in the PPT-resistant cell line. Purified GS of alfalfa has the same molecular weight. The enzyme activity of the cell extracts was determined in parallel. The specific GS-activity in the resistant cells was 5–10 fold higher than in wild type cells. The specific activity of GS in the PPT-resistant cell lines is in the same order of magnitude as in root nodule tissue of alfalfa, which, as all nodule tissues of efficiently dinitrogen fixing legumes, has high GS-activity. Measurements of the GS activity in the presence of various amounts of phosphinothricin revealed the same degree of enzyme inhibition by PPT in both cell types, suggesting that no structural change of the GS-protein had occurred during the selection of the resistant variant.

Messenger RNA was isolated from wild type and resistant cells using a guanidium isothiocyanate RNA-extraction method, followed by the separation of the mRNA through an oligo dT-cellulose column. 4 microgram mRNA could be isolated per gram of cell material. In vitro translation of the isolated mRNA from both cell lines yielded patterns of polypeptides similar to the in vivo pattern obtained in $^{35}$S-methionine labelled extracts. This indicated that the isolated mRNA was fairly undegraded. While the in vivo labelled proteins showed a striking difference in the amount of the 40–42 KD polypeptide, the difference between wild type and variant cell line in the in vitro translated protein patterns was not pronounced.

First and second strand cDNA were synthesized from the mRNA population of the PPT-resistant variant. After $S_1$-cleavage and poly C-tailing of the cDNA, the DNA was annealed to poly G-tailed pBR 322 vector DNA. E. coli strain MC1061 wa transformed with the recircularized vector.

$3.5 \times 10^4$ colonies were obtained per mg of annealed vector DNA. 80% of the colonies were ampicillin (amp) sensitive, and 50% of the amp sensitive clones had inserts which could be detected by Pst digestion of the plasmids. 10% of the inserts were longer than 1,000 base pairs.

1,800 colonies were grown on nitrocellulose filters and the filters were probed with $^{32}$P-labelled first strand cDNA probe having increased percentage of GS-specific sequences. Amongst such clones it was expected to find a GS-specific cDNA clone. A GS-cDNA clone from a Phaseolus cDNA library prepared from mRNA of root nodules was obtained from an outside source. This GS-cDNA clone enabled the identification of one alfalfa cDNA clone in the cDNA library, which hybridized strongly to the Phaseolus GS-DNA.

The insert DNA of the alfalfa GS-cDNA clone was sequenced. The alfalfa and the Phaseolus GS-cDNAs were then used as probes to characterize the difference between the wild alfalfa cells and the variant, GS-overproducing cells.

Total genomic DNA was prepared from alfalfa leaves, from wild-type cell line and from three sublines of the resistant cell line which had been selected in presence of $6 \times 10^{-4}$M, $2 \times 10^{-3}$M and $3 \times 10^{-3}$M L-phosphinothricin. The DNA was digested with Bam HI, Eco RI, and HindIII, and a combination of 2 enzymes. After agarose gel electrophoresis of the digested DNAs, the DNA fragments were transferred onto nitrocellulose filters by Southern blotting. The filter-bound DNA was hybridized with $^{32}$P-labelled cDNA inserts of the alfalfa and the Phaseolus GS-clones. DNA of the same size hybridized with both probes. One predominant band hybridizes with the same intensity in all 5 DNA samples with the alfalfa probe. A second band, which is barely visible in the wild type DNA digest, strongly hybridizes with DNA of the resistant cell lines. The highest degree of hybridization was observed with DNA of the highly resistant cell lines, indicating amplification of a DNA fragment during the development of the resistance. The alfalfa cDNA probe strongly hybridized to the amplified DNA fragment and, to a lesser extent, to the non-amplified DNA with GS homology.

In order to confirm the reason why the variant alfalfa cell line had become resistant to PPT, both Northern and Southern blots were repeated using wild type and variant cell lines. The Northern blot indicated that there is an increase of about 8 fold in glutamine synthetase mRNA from wild type. When Southern blots were done using genomic DNA from both cell lines, there was a clear indication of gene duplication of glutamine synthetase in the mutant alfalfa cell line. The duplication seems to be 5 to 15 fold above the unduplicated glutamine synthetase gene as estimated by hybridization. It also appeared to be an exact duplication, that is, only one band increased in hybridization by 7 to 11 fold.

EXAMPLE 2

Isolation and Characterization of Glutamine Synthetase from the PPT-Resistant Cell Culture.

Materials and Methods

CNBr Cleavage

Glutamine synthetase (12 nmol) was dissolved in 1 mL of 70% formic acid, 5 mg CNBr was added, and the cleavage proceeded for 24 hr at room temperature (Gross, *Meth. Enzymol.*:238–255 (1967)). After dilution with distilled water (6 mL), the mixture was lyophilized twice.

High Performance Liquid Chromatography of CNBr Peptides

Reverse-phase high performance liquid chromatography (HPLC) was carried out on an Ultrapore RPSC (0.46 ID × 7.5 cm) at 40° C. using 0.1% trifluoroacetic acid (TFA) (Bennett et al., *Biochem. J.* 168:9–13 (1977)) and a linear gradient of 0–60% acetonitrile (30 min; flow rate, 0.5 mL/min). The CNBr peptides were dissolved in the minimum volume of 6M guanidine hydrochloride in 0.1% TFA. Chromatographic peaks from several separations were collected manually, pooled, and lyophilized. Detection was at 214 nm using a Beckman 160 detector.

Amino acid analysis

Amino acid compositions were determined after acid hydrolysis of samples in sealed, evacuated tubes (Pyrex ®, culture, rimless, 6 × 50 mm) at 110° C. for 24 hr in constant boiling HCl (0.025 mL) (Moore, *Chemistry and Biology of Peptides*. Ann Arbor Science, Ann Arbor, Mich., 629–653 (1972)). Using a Beckman 6300 amino acid analyzer equipped with two Hewlett-Packard 3390A integrators, ninhydrin and two channel (440 and 570 nm) integration provided analysis of all amino acids, except tryptophan, cysteine, asparagine, and glutamine, with confidence values of 1-7% at 100 pmol/amino acid, and with a lower limit of detection of 25 pmol. Analyses were done 3-5 times on each sample and background controls.

Protein sequence analysis

Automated Edman degradation was performed with an Applied Biosystems 470A sequencer. The sequence program was developed earlier for the gas-liquid solid phase peptide and protein sequencer (Hewick et al., *J. Biol. Chem.* 256:7990-7997 (1981)). The program contains one coupling step (44.C, 26 min) and a single cleavage step (44° C., 6.7 min). Automated conversion of the 2-anilino-5-thiazolinone derivatives (Pth-amino acids) uses 25% trifluoroacetic acid (50 C, 33 min). Polybrene® (1.5 mg) (Tarr et al., *Anal. Biochem.* 84:622-627 (1978); Klapper et al., ibid., 85:126-131 (1978)) was added to the glass filter disc in the cartridge prior to degradation of protein or peptides, and five sequence cycles were run to reduce contaminants derived from Polybrene®. Angiotensin II (1 nmol) was added to the cartridge filter, and ten degradative cycles were completed. Sequencing of angiotensin allowed an assessment of the chemical and mechanical operation of the sequencer prior to the sequencing of an unknown. Protein sequence analysis of sperm whale apomyoglobin (100-200 pmol) routinely demonstrated an initiated yield of 45-55%, average repetitive yield of 92-93%, and an average lag per cycle of 2-3%. All Pth-amino acids were identified by reverse-phase high performance liquid chromatography on a cyano column (0.45×25 cm) using a 15 mM sodium acetate buffer (pH 5.5), and a complex gradient of acetonitrile/methanol (92.5:7.5, v/v), based on a system developed by Hunkapiller and Hood, *Methods Enzymol.* 91:486-493 (1983). This HPLC system separated the Pth-amino acids and internal standard (methyl ester of Pth-Glu) from the major contaminants: a dithiothreitol-adduct, N-dimethyl-N-phenylthiourea, and diphenylthiourea. Methionine and proline were not routinely separated, but a modification of the gradient separated these two Pth-amino acids. Internal standard (200 pmol) was added to each cycle collection, and the samples were dried in a Speedvac Concentrator with an RH100-6 rotor. The dried samples were dissolved in 0.025 mL of water/acetonitrile (80:20, v/v), and an aliquot (0.017 mL) (68% of total sample) injected automatically. The Pth-amino acids were detected by UV absorbance at 254 nm using a Beckman 160 detector.

Purification Scheme

The process of purification is briefly summarized in the following scheme: 100 gm. frozen cells

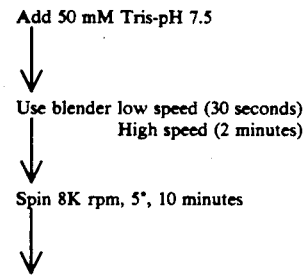

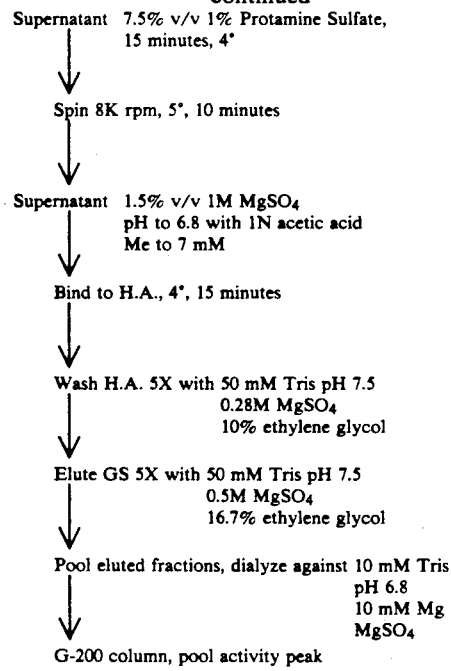

100 grams of frozen variant alfalfa tissue culture cells were mixed with dry ice and ground to a fine powder in a blender. After thawing, the mixture was spun at 8,000 rpm at 4° for 20 minutes. Protamine sulfate precipitation was carried out on the supernatant to remove nucleic acid. The MgSO₄ concentration was brought to 10 mM, the β-mercaptoethanol to 7 mM, and the pH adjusted to 6.8 with 1N acetic acid. The crude extract was bound to hydroxylapatite (H.A.). The H.A. was washed batchwise 5 times with 10 mM Tris, pH 7.5, 0.28M MgSO₄, and 10% ethylene glycol. Glutamine synthetase was eluted by bringing the MgSO₄ concentration to 0.5M. Five batch elutions were done. After dialyzing against 10 mM Tris, pH 7.5, 10 mM MgSO₄, it was loaded onto a G-200 column. Fractions with good glutamine synthetase activity were pooled. By SDS acrylamid gel and silver staining, the protein was better than 95% pure. An amino acid composition showed the composition of alfalfa glutamine synthetase to be nearly the same as that of a published composition from soy bean (Table 1).

TABLE 1

| Amino Acid Composition of Alfalfa Glutamine Synthetase | | | |
|---|---|---|---|
| Amino Acid | Soy Bean* Root (mole %) | Pea Leaf (mole %) | Alfalfa (mole % + C.V.) |
| Ala | 8.4 | 6.9 | 8.7 (+0.4) |
| Arg | 5.6 | 4.0 | 5.0 (±0.5) |
| Asx | 10.4 | 10.7 | 11.4 (±0.6) |
| Cys | 0.8 | N.D. | N.D. |
| Glx | 10.0 | 10.1 | 9.9 (±0.5) |
| Gly | 10.6 | 19.1 | 13.5 (±0.7) |
| His | 2.2 | 3.6 | 3.1 |
| Ile | 6.6 | 5.6 | 8.4 (±0.4) |
| Leu | 6.7 | 6.5 | 7.6 (±0.9) |
| Lys | 5.9 | 5.7 | 6.8 (+0.3) |
| Met | 1.6 | N.D. | 0.6 (±0.3) |
| Phe | 2.8 | 2.6 | 2.3 |
| Pro | 6.1 | 8.8 | 8.0 (+0.6) |
| Ser | 5.4 | 7.8 | 6.5 (±0.4) |
| Thr | 5.1 | 4.9 | 5.6 (±0.3) |
| Trp | 1.5 | N.D. | N.D. |
| Tyr | 3.9 | 0.5 | 3.4 (±0.7) |

TABLE 1-continued

| Amino Acid Composition of Alfalfa Glutamine Synthetase | | | |
|---|---|---|---|
| Amino Acid | Soy Bean* Root (mole %) | Pea Leaf (mole %) | Alfalfa (mole % + C.V.) |
| Val | 6.3 | 4.8 | 4.4 (±1.5) |

*R.H. McParland et al., Biochem. J. (1976) 153:597-606
N.D. = Not determined
C.V. = Confidence Value (S.D./mean)

Sequencing

A first attempt at sequencing was initiated using the purified native protein. There was no obtainable sequence, indicating that the $NH_2$-terminal was naturally blocked. A CNBr cleavage was carried out, and the fragments were separated by HPLC. The amino acid composition of the protein indicated that there were only two to five methionines. Two of the HPLC separated CNBr fragments yielded useful sequence information.

Sequencing of purified glutamine synthetase fragment was then carried out. The results are as follows:

Arg—Glu—Asp—Gly—Gly—Tyr—Glu—Val—Ile—
Leu—Lys—Ala—Ile—Glu—Lys—Leu—Gly—Lys—
Lys—(Glu/His)—Lys—Glu—His—Ile—Ala—
Ala—Tyr—Gly—Gly—Gly—Asn

This sequence corresponds to part of the sequence obtained from the complete variant alfalfa cDNA clone, with the exception of the circled Gly residue. The deduced protein sequence is shown on the following page.

```
  1  ATG TCT CTC CTT TCA GAT CTT ATC AAC CTT GAC CTC TCC GAA ACC ACC GAG AAA ATC ATC GCC GAA TAC ATA TGG   75
     Met Ser Leu Leu Ser Asp Leu Ile Asn Leu Asp Leu Ser Glu Thr Thr Glu Lys Ile Ile Ala Glu Tyr Ile Trp

76  ATT GGT TCT GGT TTC GAC TTG AGG AGA ACT AGG ACT CTA CCA GGA AAA GCA CCT ACT GAC CCT TCA CAG CTT  150
     Ile Gly Ser Gly Phe Asp Leu Arg Arg Thr Arg Thr Leu Pro Gly Lys Ala Pro Thr Asp Pro Ser Gln Leu

151  CCC AAG TGG AAC TAT GAT TCC AGC ACA GGT CAA GCT CCT GGA GAA GAT AGT GAA GTT ATT ATC TAC CCA CAA  225
     Pro Lys Trp Asn Tyr Asp Ser Ser Thr Gly Gln Ala Pro Gly Glu Asp Ser Glu Val Ile Ile Tyr Pro Gln

226  GCC ATT TTC AGA AAG GAC TTT AGA AGG GGT AAC AAT ATC TTG GTT ATG TGT GAT GCA TAC ACT CCA GCT GGA GAG  300
     Ala Ile Phe Arg Lys Asp Phe Arg Arg Gly Asn Asn Ile Leu Val Met Cys Asp Ala Tyr Thr Pro Ala Gly Glu

301  CCC ATT CCC ACC AAC AAG AGA CAT GCA GCT AAG ATT TTC AGC CAT CCT GAT GTT GCT GAA GTA CCA TGG  375
     Pro Ile Pro Thr Asn Lys Arg His Ala Ala Lys Ile Phe Ser His Pro Asp Val Ala Glu Val Pro Trp

376  TAT GGT ATT GAG CAA GAA TAC ACC TTG CAG AAA GAC ATC AAT TGG CCT CTT GGT TGG CCA GTT GGT GGT TTT  450
     Tyr Gly Ile Glu Gln Glu Tyr Thr Leu Gln Lys Asp Ile Asn Trp Pro Leu Gly Trp Pro Val Gly Gly Phe

451  CCT GGA CCT CAG GGA CCA TAC TAT TGT GGA GCT GGT GCT GAC ATT GTT GGC CGT GTT GAC ATT GTT GAC TCA CAT  525
     Pro Gly Pro Gln Gly Pro Tyr Tyr Cys Gly Ala Gly Ala Asp Ile Val Gly Arg Val Asp Ile Val Asp Ser His

526  TAC AAA GCC TGT CTT TAT GCC GGC ATC AAC AGT GGA GAT GAG ATA TGG GTT GCT CGT TAC ATT TTG GAG AGG ATC ACT  600
     Tyr Lys Ala Cys Leu Tyr Ala Gly Ile Asn Ser Gly Asp Glu Ile Trp Val Ala Arg Tyr Ile Leu Glu Arg Ile Thr

601  CAA GTT GGT GTG GTG CTT TCC TTT GAC CCA AAA CCA ATT AAG GGT GAT TGG AAT GGT GCT GGT GCT CAC ACA  675
     Gln Val Gly Val Val Leu Ser Phe Asp Pro Lys Pro Ile Lys Gly Asp Trp Asn Gly Ala Gly Ala His Thr

676  GAG GTT GCT GGT ACC AAG TCT ATG AGA GAA GAT GGT GGG TAT GAA GTC ATC TTG AAA GCA ATT GAG AAG CTT GGG AAG  750
     Glu Val Ala Gly Thr Lys Ser Met Arg Glu Asp Gly Gly Tyr Glu Val Ile Leu Lys Ala Ile Glu Lys Leu Gly Lys

751  AAT TAC AGC TAC AAG GAG GAT CCA GAT GGT GGC TAT ATT TTT GAC GAG GGT TAT TGG AAG CAT GAG ACA GCT GAC  825
     Asn Tyr Ser Tyr Lys Glu Asp Pro Asp Gly Gly Tyr Ile Phe Asp Glu Gly Tyr Trp Lys His Glu Thr Ala Asp

826  AAG CAC AAG GAG CAC ATT GCT GCT TAT GGA GAA GGC AAC GAG CGT TTG ACA GGA CGA CAT GAG CGA GAC GCT GGA AAG  900
     Lys His Lys Glu His Ile Ala Ala Tyr Gly Glu Gly Asn Glu Arg Leu Thr Gly Arg His Glu Arg Asp Ala Gly Lys

901  ATT AAC ACC TTC TTA TGG GGT GTT GCA AAC CGT GGT GCG ATT GGA AGG GAC ACA GAG AAA GCA GGG  975
     Ile Asn Thr Phe Leu Trp Gly Val Ala Asn Arg Gly Ala Ile Gly Arg Asp Thr Glu Lys Ala Gly
```

-continued

```
 976 AAA GGT TAT TTC GAG GAT AGG AGG CCA TCA TCT AAC ATG GAT CCA TAT GTT GTT ACT TCC ATG ATT GCA GAC ACC 1050
     Lys Gly Tyr Phe Glu Asp Arg Arg Pro Ser Ser Asn Met Asp Pro Tyr Val Val Thr Ser Met Ile Ala Asp Thr
1051 ACC ATT CTC TGG AAA CCA TAA 1071
     Thr Ile Leu Trp Lys Pro End
```

Preparation of a Functional Genomic Sequence Coding for Glutamine Synthetase

Total genomic DNA was obtained from the alfalfa tissue culture using a protocol similar to that used to obtain that of Phaseolus root nodules (Cullimore, J. D., and Miflin, B. J., *FEBS Letters* 58:107–112 (1983)), and digested totally with Bam HI. The material was then size fractionated into a potassium acetate 5–20% gradient and separated into aliquots. Each aliquot was then run on a 1% agarose gel and probed in a Southern transfer system with cDNA glutamine synthetase probe obtained from a Pst cut of the coding sequence probe shown above. Positively hybridizing fractions, selected for fragments of size greater than or equal to 4 Kb, were ligated to a BV-2 lambda vector. 100,000 phages were plated and probed with the glutamine synthetase cDNA probe as above. Four positive plaques were obtained. These were then grown and plaque-hybridization purified for 3–4 rounds. A purified 4 Kb genomic clone was isolated and religated into M13mp9. This clone was sequenced from both ends. In addition, the clone was also fragmented with Hae III, subcloned into M13mp9 and again sequenced.

In this manner, this 4 Kb 5' fragment (as well as part of an 8 Kb 3' fragment also obtained from the digestion of the genomic DNA) was completely sequenced. Both of these fragments together provide a complete functional gene, the reading frame being predicted from the protein sequence information at hand, the known GS molecular weight and the relative incident of stop triplets in the three possible reading frames. The complete genomic sequence for glutamine synthetase, including intron and exon regions, is shown in FIG. 4. With a complete functional sequence for GS at hand, the same can be expressed by any of the methods described previously.

EXAMPLE 3

Genetic Construct for GS Overproduction

Figure 5:
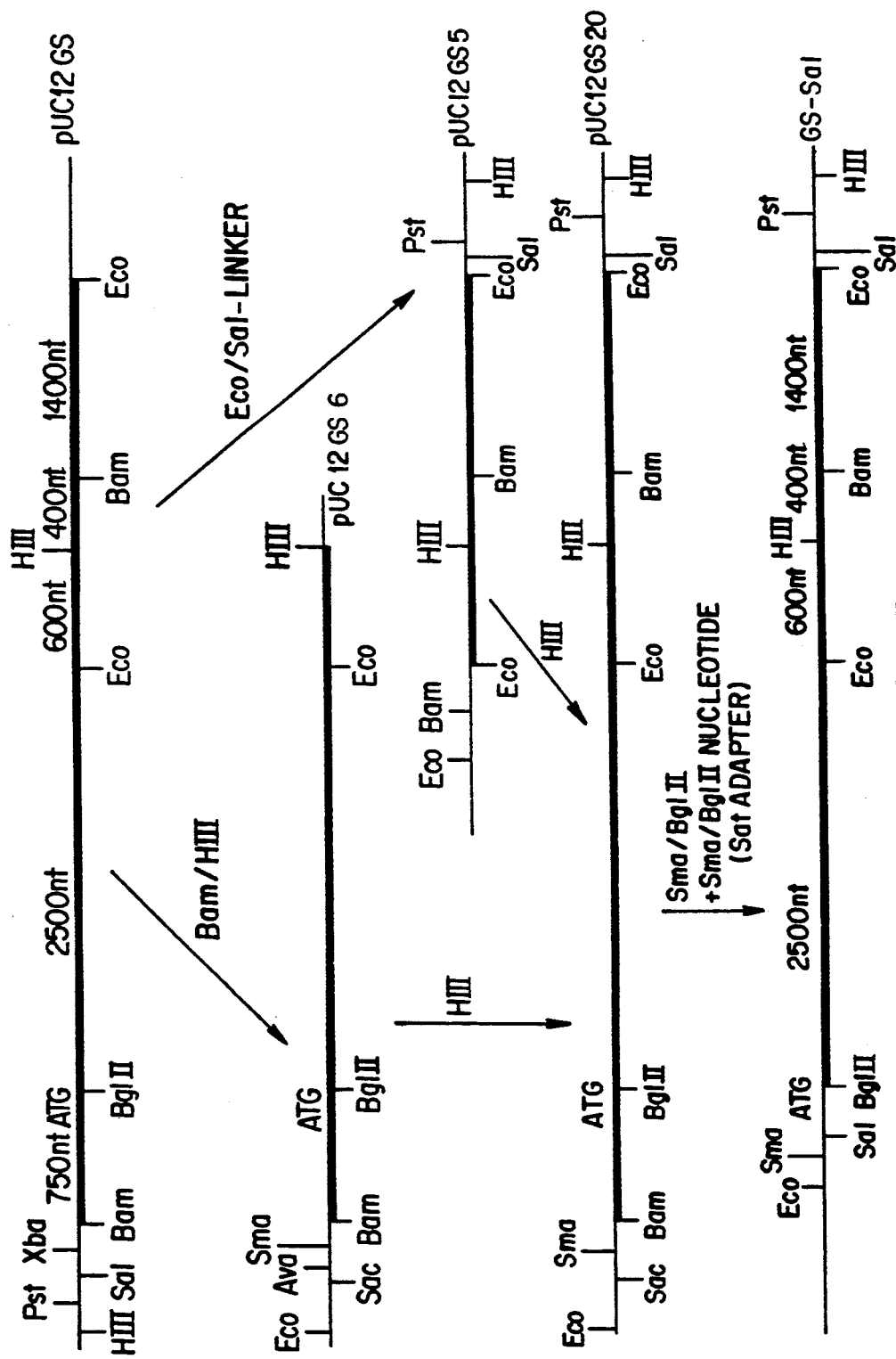
FIG. 5 shows individual cloning steps for the GS gene from *Mendicago sativa*, then used in a construct for overproduction of GS. (See Example 3.)

The individual cloning steps for the glutamine synthetase gene from *Medicago sativa* (Tischer et al., *Gen. Genet.* 203:221 (1986)) are shown in FIG. 5. The gene, starting with the 6th nucleotide in front of the translation start codon ATG and ending behind a 3' non-translated region approximately 1200 nucleotides long, was able to be isolated with the restriction enzyme Sal I in a single fragment.

The promoters of the following genes were linked with the glutamine synthetase gene:

a) Gene 1' of the TR-DNA from *Agrobacterium tumefaciens* A6 (Velten et al., *EMBO J.* :2723 (1984));

b) Gene 2' of the TR-DNA from *Agrobacterium tumefaciens* A6 (Velten et al., *EMBO J.* 3:2723 (1984));

c) ST-LS1, a leaf and stalk-specific, photoregulated gene from *Solanum tuberosum* (Eckes et al., *Mol. Gen. Genet.* 205:15 (1986)); and d) 35S-transcript from Cauliflower Mosaic Virus (Pietrzak et al., *Nucl. Acids Res.* 14:5857 (1986)).

The promoters of the genes cited under a) and b) 1. were cloned into the plasmid pPCV 701 which is useful for subsequent plant transformation (Koncz et al., *Proc. Natl. Acad. Sci. USA* 84:131 (1987)). The ST-LS 1 promoter was cloned as an EcoRI-SmaI fragment into the polylinker of the intermediary *E. coli* vector pMPK 110 (Peter Eckes, Dissertation, University of Cologne, 1985). The 35 S promoter was likewise cloned as an EcoRI-SmaI fragment approximately 540 bp long into pMPK 110 via EcoRI-SmaI.

A SalI cut is located behind each of the promoters cited under a), c) and d) with the insertion sequences listed in the following, so that the modified glutamine synthetase gene (GS gene) was able to be inserted into this cut in the proper orientation.

The fusion portions between the promoters and the modified GS gene are as follows:

TR1: (promoter; 400 nucleotides) -
AAACACCGATATTCATTAATCTTATCTAGTTTCTCAAAAAAA
TTCATATCTTCCACACGTGGATCGATCC<u>GTCGAC</u>
(SalI)

ST-LS1: (promoter; approx. 1600 nucleotides) -
AAGAAGAAAAAAGGTGGGGATCC<u>GTCGAC</u>
               |          (SalI)
     (MboII/SmaI)

35S: (promoter; approx. 500 nucleotides) -
GGGTA<u>CCCGGGG</u>ATCCTCTAGA<u>GTCGAC</u>
     (SmaI)            (SalI)

A BamHI restriction cut is behind the promoter cited under b). After restriction digestion, the projecting DNA ends were filled up with DNA polymerase (Klenow fragment), just like the SalI ends of the GS gene. The GS gene was ligated behind the TR2 promoter via the blunt ends of the DNA fragments created in this manner.

The promoter-GS constructs (c) and (d) created in this manner were transferred with the aid of the intermediary *E. coli* vector pMPK110 into *Agrobacterium tumefaciens* (Peter Eckes, Dissertation, Univ. of Cologne, p. 91 ff., 1985). This so-called conjugation was performed according to the method described by Van Haute et al. (*EMBO J.*:441 (1983)). The gene was thereby integrated with its regulation signals by means of homologous recombination via the sequences of vector pBR322 contained in the pMPK110 vector and in the Ti-plasmid pGV3850 Km (Jones et al., *EMBO J.* :2411 (1985)) into the Ti plasmid. The promoter-GS construct was also localized on the Ti plasmid pGV3850Km in addition to the resistance gene against the antibiotic Kanamycin, which gene was already present previously and is active in plants. Both genes were transferred by means of the so-called "leaf disc" transformation method into tobacco plants (Horsch et al., *Science* 227:1229 (1985)).

The promoter GS constructs (a) and (b) were mobilized on the transformation plasmid pPCV 701 (see above) into *Agrobacterium tumefaciens* pGV3101, according to the method described by Koncz et al. (*Mol. Gen. Genet.* 204:383 (1986)). Using the "leaf disc" method cited above, the promoter-GS constructs in Agrobacterium were transferred, together with the Kanamycin-resistance gene already localized on the pPCV701 plasmid as selectable marker, into tobacco plants.

Transformed shoots were selected on the basis of the transferred resistance to Kanamycin, and were regenerated into complete plants. The presence and expression of the GS gene could be demonstrated by DNA analysis ("Southern blotting"), RNA analysis ("Northern blotting") and protein analysis ("Western blotting").

The transferred GS gene from *Medicago sativa* is expressed approximately 10 times stronger on the RNA level in transformed tobacco plants than in Medicago itself. The GS protein constitutes up to 5% of the total protein in transformed plants. The glutamine synthetase activity is likewise elevated, as is apparent from the following Table 2:

TABLE 2

| Specific Glutamine Synthetase Activity in Different Plants | |
|---|---|
| Plant | Activity (NKAT/mg total protein) |
| alfalfa leaf (wild type) | 0.4 |
| tobacco leaf (wild type) | 3.2 |
| tobacco leaf (produced according to Example 3) | 9.5 |

Having now fully described this invention it will be understood that the same can be operated within a broad and equivalent range of structures, products, processes, and uses without affecting the spirit or scope of the invention or any embodiment thereof.

What is claimed as new and intended to be covered by Letters Patent of the United States is:

1. A plant cell which is stably resistant to a herbicidal glutamine synthetase (GS) inhibitor, wherein said resistance is retained in the absence of said inhibitor, wherein said resistance is caused by plant cell levels of GS activity which, when present in an otherwise herbicidal GS-inhibitor sensitive plant cell, render said cell substantially resistant to said herbicidal GS-inhibitor.

2. The resistant plant cell of claim 1, wherein said levels of GS activity are present by virtue of said plant cell having a significantly larger number of copies of the naturally occurring GS gene therein, than the corresponding sensitive plant cell.

3. The plant cell of claim 2, wherein the number of copies of the naturally occurring GS gene in said plant cell is such that the levels of GS activity produced therefrom render said cell substantially resistant to said herbicidal GS-inhibitor.

4. The plant cell of any of claims 1 or 2, wherein the naturally occurring gene for GS in said plant cell is substantially amplified.

5. The plant cell of claim 1 carrying a genetic sequence combination which comprises:
   (a) a first genetic sequence coding for glutamine synthetase (GS) functional in said plant cell, operably linked to
   (b) a second genetic sequence capable of increasing the levels of expression of said first genetic sequence such that when such combination is present in an otherwise herbicidal GS-inhibitor sensitive plant cell, said cell is substantially resistant to said herbicidal GS-inhibitor.

6. The plant cell of claim 5, wherein said combination is integrated in the genome of said plant cell.

7. The plant cell of claim 5, wherein said combination is present in a Ti plasmid of *Agrobacterium tumefaciens*.

8. The plant cell of any of claims 1, 2, 3, 5, 6 or 7, wherein said herbicidal GS-inhibitor is PPT.

9. A genetic sequence combination operable in a given plant cell which comprises:
   (a) a first genetic sequence coding for glutamine synthetase functional in said plant cell, operably linked to
   (b) a second genetic sequence capable of increasing the levels of expression of said first sequence such that when said combination is present in an otherwise herbicidal GS-inhibitor sensitive plant cell, said cell is substantially resistant to said herbicidal GS-inhibitor.

10. The genetic sequence combination of claim 9, wherein said first genetic sequence codes for genomic glutamine synthetase.

11. The genetic sequence combination of claim 9, wherein said second genetic sequence is a promoter.

12. The genetic sequence combination of any of claims 9-11, which is integrated in the genome of said plant cell.

13. The genetic sequence combination of any of claims 9-11, which is present in the Ti plasmid of Agrobacterium tumefaciens.

14. The genetic sequence combination of any of claims 9-11, wherein said herbicidal GS-inhibitor is PPT.

15. A method of conferring herbicidal GS-inhibitor resistance to an otherwise herbicidal GS-inhibitor sensitive plant cell which comprises increasing the copies of the naturally occurring GS gene present in said sensitive plant cell.

16. The method of claim 15, wherein said herbicidal GS-inhibitor resistance is PPT resistance.

17. A method of conferring herbicidal GS-inhibitor resistance to a plant cell which comprises transforming said cell with the genetic sequence combination of any of claim 9 or 10.

18. The method of claim 17 wherein said herbicidal GS-inhibitor is PPT.

19. An isolated DNA molecule comprising a eukaryotic genetic sequence coding for glutamine synthetase wherein said sequence is functional in a plant cell.

20. The molecule of claim 19, which is a vehicle capable of transforming a plant cell.

21. An isolated DNA (rDNA) molecule comprising a genetic sequence coding for glutamine synthetase, wherein said glutamine synthetase comprises the following polypeptide formula:

Met—Ser—Leu—Leu—Ser—Asp—Leu—Ile—Asn—

Leu—Asp—Leu—Ser—Glu—Thr—Thr—Glu—Lys—

Ile—Ile—Ala—Glu—Tyr—Ile—Trp—Ile—Gly—

Gly—Ser—Gly—Leu—Asp—Leu—Arg—Ser—Lys—

Ala—Arg—Thr—Leu—Pro—Gly—Pro—Val—Thr—

Asp—Pro—Ser—Gln—Leu—Pro—Lys—Trp—Asn—

Tyr—Asp—Gly—Ser—Ser—Thr—Gly—Gln—Ala—

Pro—Gly—Glu—Asp—Ser—Glu—Val—Ile—Ile—

Tyr—Pro—Gln—Ala—Ile—Phe—Lys—Asp—Pro—

Phe—Arg—Arg—Gly—Asn—Asn—Ile—Leu—Val—

Met—Cys—Asp—Ala—Tyr—Thr—Pro—Ala—Gly—
Glu—Pro—Ile—Pro—Thr—Asn—Lys—Arg—His—
Ala—Ala—Ala—Lys—Ile—Phe—Ser—His—Pro—
Asp—Val—Ala—Glu—Val—Pro—Trp—Tyr—
Gly—Ile—Glu—Gln—Glu—Tyr—Thr—Leu—Leu—
Gln—Lys—Asp—Ile—Asn—Trp—Pro—Leu—Gly—
Trp—Pro—Val—Gly—Gly—Phe—Pro—Gly—Pro—
Gln—Gly—Pro—Tyr—Tyr—Cys—Gly—Ala—Gly—
Ala—Asp—Lys—Ala—Phe—Gly—Arg—Asp—Ile—
Val—Asp—Ser—His—Tyr—Lys—Ala—Cys—Leu—
Tyr—Ala—Gly—Ile—Asn—Ile—Ser—Gly—Ile—
Asn—Gly—Glu—Val—Met—Pro—Gly—Gln—Trp—
Glu—Phe—Gln—Val—Gly—Pro—Ser—Val—Gly—
Ile—Ser—Ala—Gly—Asp—Glu—Ile—Trp—Val—
Ala—Arg—Tyr—Ile—Leu—Glu—Arg—Ile—Thr—
Glu—Val—Ala—Gly—Val—Val—Leu—Ser—Phe—
Asp—Pro—Lys—Pro—Ile—Lys—Gly—Asp—Trp—

Asn—Gly—Ala—Gly—Ala—His—Thr—Asn—Tyr—
Ser—Thr—Lys—Ser—Met—Arg—Glu—Asp—Gly—
Gly—Tyr—Glu—Val—Ile—Leu—Lys—Ala—Ile—
Glu—Lys—Leu—Gly—Lys—His—Lys—Glu—
His—Ile—Ala—Ala—Tyr—Gly—Glu—Gly—Asn—
Glu—Arg—Arg—Leu—Thr—Gly—Arg—His—Glu—
Thr—Ala—Asp—Ile—Asn—Thr—Phe—Leu—Trp—
Gly—Val—Ala—Asn—Arg—Gly—Ala—Ser—Ile—
Arg—Val—Gly—Arg—Asp—Thr—Glu—Lys—Ala—
Gly—Lys—Gly—Tyr—Phe—Glu—Asp—Arg—Arg—
Pro—Ser—Ser—Asn—Met—Asp—Pro—Tyr—Val—
Val—Thr—Ser—Met—Ile—Ala—Asp—Thr—Thr—
Ile—Leu—Trp—Lys—Pro

22. A herbicidal GS-inhibitor resistant plant comprising a cell according to any of claims 1, 2, 3, 5, 6 or 7, wherein said resistant plant is a dicotyledonous plant.

23. The method of claim 22, wherein said herbicidal GS-inhibitor is PPT.

24. A plant comprising the cell of claim 5, wherein said plant is a dicotyledonous plant.

* * * * *